United States Patent [19]

Miller

[11] Patent Number: 5,801,293

[45] Date of Patent: Sep. 1, 1998

[54] METHOD OF ISOMERIZING OLEFINS

[75] Inventor: Stephen J. Miller, San Francisco, Calif.

[73] Assignee: Chevron U.S.A. Inc., San Francisco, Calif.

[21] Appl. No.: 780,197

[22] Filed: Jan. 10, 1997

Related U.S. Application Data

[60] Provisional application No. 60/012,313, Feb. 26, 1996.

[51] Int. Cl.$^6$ .................................................. C07C 41/06
[52] U.S. Cl. .................... 568/697; 585/614; 585/649; 585/616; 585/601; 585/654
[58] Field of Search .................... 568/697; 585/614, 585/616, 601, 649, 654

[56] References Cited

U.S. PATENT DOCUMENTS

| | | | |
|---|---|---|---|
| 2,537,283 | 1/1951 | Schaad | 260/683.2 |
| 3,211,801 | 10/1965 | Holm et al. | 260/683.2 |
| 3,270,085 | 8/1966 | Noddings et al. | 260/683.2 |
| 3,304,343 | 2/1967 | Mitsutani | 260/683.2 |
| 3,327,014 | 6/1967 | Noddings | 260/683.2 |
| 3,448,164 | 6/1969 | Holm et al. | 260/683.2 |
| 4,340,465 | 7/1982 | Miller et al. | 208/120 |
| 4,368,114 | 1/1983 | Chester et al. | 208/120 |
| 4,593,146 | 6/1986 | Johnson et al. | 585/667 |
| 4,814,519 | 3/1989 | Harandi et al. | 568/697 |
| 5,132,484 | 7/1992 | Gajda | 585/667 |
| 5,191,146 | 3/1993 | Gajda et al. | 585/667 |
| 5,238,541 | 8/1993 | Marquez et al. | 203/56 |
| 5,238,889 | 8/1993 | Falling et al. | 502/24 |
| 5,387,723 | 2/1995 | Knifton et al. | 568/698 |
| 5,420,360 | 5/1995 | Chin et al. | 568/697 |

FOREIGN PATENT DOCUMENTS

| | | | |
|---|---|---|---|
| 0 026 041 A1 | 1/1981 | European Pat. Off. | 41/6 |
| 0026041 | 4/1981 | WIPO . | |

Primary Examiner—Gary Geist
Assistant Examiner—Sreeni Padmanabhan
Attorney, Agent, or Firm—Timothy J. Hadlock

[57] ABSTRACT

The invention includes a method for skeletal isomerization of $C_{4-5}$ olefins. The method includes contacting in a FCC zone, at FCC conditions, an n-$C_{4-5}$ olefins-containing etherification zone raffinate, with an FCC catalyst, where at least a portion of the n-$C_{4-5}$ olefins in the n-$C_{4-5}$ olefins-containing etherification zone raffinate are converted to iso-$C_{4-5}$ olefins.

18 Claims, 2 Drawing Sheets

METHOD OF ISOMERIZING OLEFINS

CROSS-REFERENCE TO RELATED APPLICATIONS

This application claims priority from U.S. Provisional Application Ser. No. 60/012,313, filed Feb. 26, 1996.

FIELD OF THE INVENTION

The invention relates to a method of isomerizing olefins, especially a method of making ethers from iso-olefins.

BACKGROUND OF THE INVENTION

A. The Need for Oxygenates

The widespread removal of lead antiknock additive from gasoline and the rising fuel-quality demands of high-performance internal-combustion engines have compelled petroleum refiners to install new and modified processes for increased "octane," or knock resistance, in the gasoline pool. Refiners have relied on a variety of options to upgrade the gasoline pool, including higher-severity catalytic reforming, higher FCC (fluid catalytic cracking) gasoline octane, isomerization of light naphtha and the use of oxygenated compounds. Such key options as increased reforming severity and higher FCC gasoline octane result in a higher aromatics content of the gasoline pool, through the production of high-octane aromatics at the expense of low-octane heavy paraffins. Current gasolines generally have aromatics contents of about 30% or higher, and may contain more than 40% aromatics.

Currently, refiners are faced with the prospect of supplying reformulated gasoline to meet tightened automotive emission standards. Reformulated gasoline would differ from the existing product in having a lower vapor pressure, lower final boiling point, increased content of oxygenates, and lower content of olefins, benzene and aromatics. The oxygen content of gasoline will be 2% or more in many areas. Gasoline aromatics content is likely to be lowered into the 20–25% range in major urban areas, and low-emission gasoline containing less than 15% aromatics is being advocated for some areas with severe pollution problems.

Since aromatics have been the principal source of increased gasoline octanes during the recent lead-reduction program, severe restriction of the aromatics content will present refiners with processing problems. Currently, applicable technology includes such costly steps as recycle isomerization of light naphtha and generation of additional light olefins by FCC and isobutane by isomerization as feedstock to an alkylation unit. Increased blending of oxygenates such as methyl tertiary-butyl ether (MTBE) and ethanol will be an essential part of the reformulated-gasoline program, but feedstock supplies will become stretched. Novel processing technology is needed to support an effective program.

Oxygenates have been part of the United States gasoline strategy since the late 1970s. With the recent enactment of the Clean Air Act Amendments of 1990, the demand for oxygenates has increased again such that gasoline is now being blended to 2.7 weight percent oxygen and is being marketed in numerous metropolitan areas that have failed to meet carbon monoxide pollution FOCUS standards. In the near future, it is expected that between 30 and 60 percent of the United States gasoline pool may require oxygenates.

The most commonly used oxygenates today are methanol, ethanol, and ethers such as methyl tertiary butyl ether (MTBE). Although methanol and ethanol have high blending octanes, problems with toxicity, water miscibility, high Reid Vapor Pressure (RVP), high nitrogen oxide emissions, lower fuel efficiency, and cost have dampened industry enthusiasm for these components. As a result of the above, MTBE has become particularly attractive.

Homologues of MTBE such as ethyl tertiary butyl ether (ETBE) and tertiary amyl methyl ether (TAME) are also gaining industry acceptance. Moreover, commercial activity with respect to ETBE and TAME is expected to increase relative to MTBE, in view of recent Environmental Protection Agency decisions to reduce the RVP requirements for gasolines well below 9 psia, the blending RVP of MTBE.

TAME (tertiary amyl methyl ether) is an effective octane booster as well as a source of oxygenates in gasoline that are effective in reducing CO and hydrocarbon emissions. It is made from 2-methylbutenes and methanol. The present sources of 2-methylbutene for TAME production are mainly from by-products of steam cracker, catalytic cracker and cokers. However, these supplies are limited. Other possible sources are by isomerization of n-pentenes taken from steam or catalytic crackers and by dehydrogenation of isopentane produced by isomerization of n-pentane. Olefin isomerization processes can be directed towards either skeletal isomerization or double bond isomerization. Skeletal isomerization is concerned with reorientation of the molecular structure in respect to the formation or elimination of side chains. Double bond isomerization is concerned with relocation of the double bond between carbon atoms while maintaining the backbone of the carbon structure. Most isomerization processes give rise only to double bond isomerization.

B. Sources of Ethers

Ethers can be prepared by a number of reaction routes from various starting materials as is well known in the art. The "Williamson synthesis", for example, and the dehydration of alcohols are known methods of preparing ethers. In some petroleum refining operations, there is a significant amount of lower alkyl olefins readily available from a steam cracking plant or an FCC unit. A commonly used synthesis route for such a situation is the etherification reaction of these olefins with an alcohol in the presence of an acidic catalyst.

Ether production capacity, however, is often limited by iso-olefin feedstock availability. The reaction of tertiary olefins with alkanol to produce alkyl tertiary alkyl ether is selective with respect to iso-olefins. Linear olefins are unreactive in the acid catalyzed reaction, even to the extent that it is known that the process can be utilized as a method to separate linear and iso-olefins. The typical feedstream of FCC $C_5$ or $C_5+$ crackate used to produce tertiary alkyl ethers in the prior art and containing normal pentenes and iso-pentenes utilizes only the tertiary olefins in etherification. This situation presents an exigent challenge to workers in the field to discover a technically and economically practical means to utilize linear olefins, particularly normal pentenes, in the manufacture of tertiary alkyl ethers.

Existing patents, for example, European publication 0 026,041, describes a process for producing olefins and/or ethers of high octane number from a wide $C_2$ to $C_{10}$ olefinic stream. The wide olefinic feedstock is restructured over a zeolite catalyst to form primarily $C_4$ to $C_7$ olefins, the $C_4$ to $C_7$ iso-olefins are reacted with methanol to form high octane ethers and unreacted olefins and methanol are separated from the ether product and recycled to the restructuring operation. U.S. Pat. No. 4,814,519 shows a two-stage process for the production of ethers from olefin-containing feedstock such as from an FCC unit where the feedstock is reacted under conditions to maximize production of $C_4$–$C_5$ iso-olefins, particularly tertiary iso-olefins. The resulting iso-olefin rich product is then subjected to a catalytic etherification reaction to produce ethers such as TAME. The above art thus teaches that the amount of ether which can be produced from a mixed olefin stream is limited to the contained branched olefins. The amount of contained branched olefins in the stream is limited by the thermodynamic equilibrium condition of this source olefin stream.

Commercial MTBE and ETBE processes both utilize isobutylene as a feedstock while TAME processes utilize isoamylene as a feedstock. Isobutylene and isoamylene are generally supplied to a commercial ether process from an FCC unit, a fluidized or delayed coker, or from downstream paraffin isomerization and dehydrogenation facilities. As a result, the availability of hydrocarbons having 4 or 5 carbon atoms is limited by constraints such as, but not limited to, crude properties, FCC catalyst properties and operating conditions, coking conditions, as well as by other refinery operating constraints. The chemical mix of $C_4$ and $C_5$ paraffins, olefins, and aromatics as well as the particular mix of iso-olefins to normal olefins are similarly constrained.

The relatively high ratio of capital and operating costs to the throughput of ether product subsequently produced from the construction of new facilities for increasing ether process feedstocks further exacerbates oxygenate supply. These costs are generally attributed to the high degree of complexity and the sophisticated equipment involved. This equipment is connected to the operation of dehydrogenation or isomerization processes. Such process units include desulfurization, catalytic reactor, and hydrogen supply and recirculation systems.

The profitability of such new facilities is often dependent on the ability of the refiner to keep construction costs low and operating throughput high.

There exists a great need in the petroleum industry for a low cost method of increasing oxygenate production feedstocks. The method should overcome or avoid the obstacles described above and should be economically viable in terms of construction cost and facility utilization. Iso-olefins rarely are obtained in a refinery or petrochemical product in a ratio matching product demand. As discussed above, since ether production requires iso-olefins, there is a widespread need to increase the proportion of isobutene, isopentene and other tertiary-carbon olefins for production of MTBE, TAME and other ethers.

In contrast, oligomerization of lower olefins produces an olefinic product which has an excessive proportion of alkyl substituents for high-quality plasticizer production. Catalytic isomerization to alter the ratio of isomers is one solution to these needs. Since isomerization competes with alternative feedstock sources as a source of desired isomers, an isomerization process must be efficient and relatively inexpensive. The principal problem facing workers in the art therefore is to isomerize olefins to increase the concentration of the desired isomer while minimizing product losses to heavier or lighter products.

Processes for the isomerization of olefinic hydrocarbons are widely known in the art. Many of these use catalysts comprising phosphate. U.S. Pat. No. 2,537,283, for example, teaches an isomerization process using an ammonium phosphate catalyst and discloses examples of butene and pentene isomerization. U.S. Pat. No. 3,211,801 discloses a method of preparing a catalyst comprising precipitated aluminum phosphate within a silica gel network and the use of this catalyst in the isomerization of butene-1 to butene-2. U.S. Pat. Nos. 3,270,085 and 3,327,014 teach an olefin isomerization process using a chromium-nickel phosphate catalyst, effective for isomerizing 1-butene and higher alpha-olefins. U.S. Pat. No. 3,304,343 reveals a process for double-bond transfer based on a catalyst of solid phosphoric acid on silica, and demonstrates effective results in isomerizing 1-butene to 2-butenes. U.S. Pat. No. 3,448,164 teaches skeletal isomerization of olefins to yield branched isomers using a catalyst containing aluminum phosphate and titanium compounds.

U.S. Pat. No. 4,593,146 teaches isomerization of an aliphatic olefin, preferably 1-butene, with a catalyst consisting essentially of chromium and amorphous aluminum phosphate. It would be beneficial to have a process which increases the production of iso-olefins from an FCC unit without the cost and complexity of a separate olefin isomerization plant. The present invention provides such a process. None of the above references disclose the olefin-isomerization process using the process of the present invention. This invention relates to olefin isomerization and etherification. In one of its more specific aspects, this invention relates to selective isomerization and etherification of n-pentenes and/or n-butenes.

SUMMARY OF THE INVENTION

The invention includes a method for skeletal isomerization of $C_{4-5}$ olefins. The method includes contacting in a FCC zone, at FCC conditions, an n-$C_{4-5}$ olefins-containing etherification zone raffinate, with an FCC catalyst, where at least a portion of the n-$C_{4-5}$ olefins in the n-$C_{4-5}$ olefins-containing etherification zone raffinate are converted to iso-$C_{4-5}$ olefins.

DETAILED DESCRIPTION OF PREFERRED EMBODIMENTS

A. Steps of the Process

Figure 1:
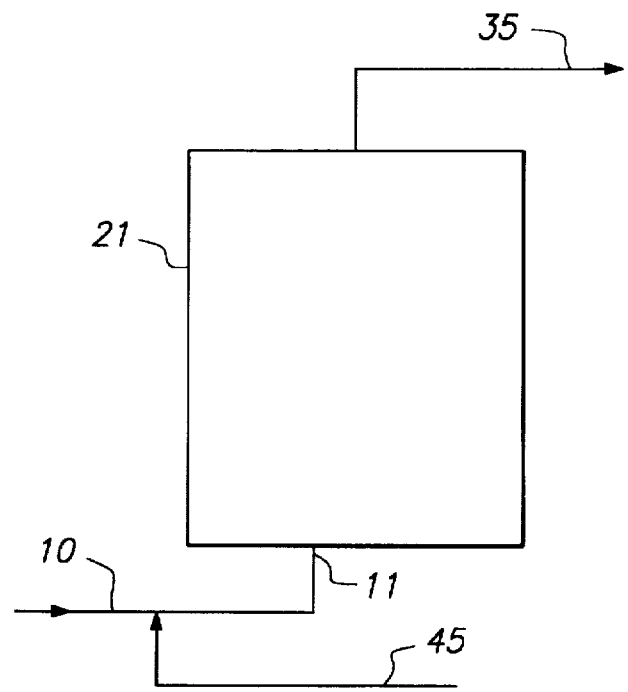
FIG. 1 depicts, in one embodiment, a schematic process flow diagram of the method of the invention where the FCC reactor feed includes an etherification zone raffinate.

Reference is made to FIG. 1 of the drawings. FCC feed stream 10 is any conventional FCC feedstock, e.g., a vacuum gas oil. FCC feed stream 10 mixes with stream 45. Stream 45 is an etherification zone raffinate containing normal $C_{4-5}$ olefins. These two streams 10 and 45 mix to form stream 11. Stream 11 is passed to FCC process unit(s) 21. The FCC process is any conventional FCC process. The units in the FCC process will typically include a FCC reactor and one or more distillation columns for fractionating the FCC reactor product. At least a portion of the normal $C_{4-5}$ olefins in the etherification zone raffinate in stream 11 are converted in the FCC unit 21 to iso-$C_{4-5}$ olefins. The FCC reactor effluent stream (not shown) contains some normal and some iso-$C_{4-5}$ olefins. One or more separation units, e.g., distillation units, separate the FCC reactor effluent into various fractions. One fraction is stream 35 which contains normal and iso-$C_{4-5}$ olefins. Stream 35 is optionally passed to an etherification unit (shown in FIGS. 2 and 3). In an etherification unit, the ethers produced are selected from MTBE and TAME, and mixtures thereof. These are the oxygenates most useful for reformulated gasolines.

Figure 2:
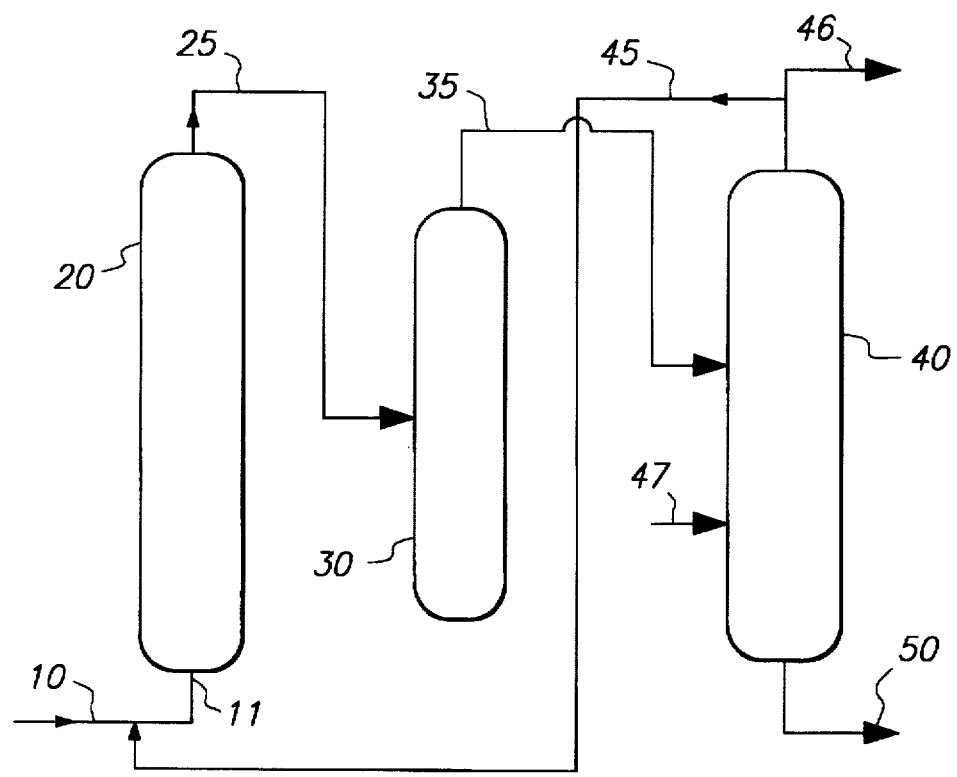
FIG. 2 depicts, in one embodiment, a schematic process flow diagram of the method of the invention where the etherification unit is a combined reactive-distillation unit.

FIG. 2 depicts the main component parts of FCC unit 21. An FCC reactor 20 and a separation unit 30 are depicted in FIG. 2. Additional units are shown as discussed below.

Various fractions are recovered from separation zone 30. One fraction is stream 35 containing normal and iso-$C_{4-5}$ olefins. These are passed to etherification-distillation unit 40. Reactive distillation occurs in etherification-distillation unit 40 to react methanol stream 47 with at least some of the iso-$C_{4-5}$ olefins to produce ethers. Stream 50 contains the product ethers and etherification-distillation unit 40 raffinate stream 45 contains normal $C_{4-5}$ olefins. Where etherification-distillation unit 40 produces MTBE the normal $C_{4-5}$ olefins in stream 45 will be butenes. Where etherification-distillation unit 40 produces TAME the normal $C_{4-5}$ olefins in stream 45 will be pentenes. Stream 45 is recycled to mix with stream 10. Streams 45 and 10 mix to form stream 11. Stream 11 is passed to FCC unit 20. Stream 46 contains any portion of the etherification unit raffinate not recycled to FCC unit 20.

At least a portion of the normal $C_{4-5}$ olefins in stream 45 fed to FCC unit 20 are converted to iso-$C_{4-5}$ olefins. The iso-$C_{4-5}$ olefins produced in FCC unit 20 are passed via stream 25 for eventual use in etherification unit 40.

By this method, iso-olefin production from the FCC unit is increased. Adding the etherification zone raffinate to the FCC reactor increases the amount of n-olefins available for conversion to iso-olefins in the FCC reactor. Accordingly, where there is a need for greater amounts of iso-olefins for etherification or other processes, the instant process obviates the need for a separate and expensive isomerization unit.

Optionally, in addition to the FCC catalyst fed to FCC unit 20, a catalyst additive is added to the FCC catalyst. This additive is an olefin isomerization catalyst. The olefin isomerization catalyst may include any known catalyst which will catalyze isomerization of normal $C_{4-5}$ olefins under FCC conditions. The FCC catalyst does perform some n-olefin isomerization in addition to its cracking function. Thus, the additive catalyst should be one more selective to isomerization of n-olefins than the FCC catalyst. If the additive catalyst were less selective, there would no benefit in using an additive catalyst in comparison to the FCC catalyst for obtaining increased isomerization of n-olefins. These isomerization catalysts optionally include an intermediate pore zeolite, e.g., a ZSM-5 type zeolite having a $SiO_2/Al_2O_3$ mole ratio greater than about 40, preferably greater than about 200, or more preferably greater than about 500.

The weight percent of the ZSM-5 zeolite based on the weight of the total amount of catalyst fed to the FCC unit is from about 0.1 to about 4, preferably from about 0.2 to about 2. This calculation is exclusive of the binder for the ZSM-5 zeolite since different binder-zeolite mixes will contain different percents of ZSM-5 zeolite and binder.

The amount of the etherification raffinate recycled in stream 45 to the FCC reactor 20 is subject to some constraints. For any given maximum overall feedrate capacity for an FCC reactor, the amount of recycled etherification zone raffinate should not be so great as to require reducing the amount of FCC feedstock below its desired feedrate. Paraffin build-up is another limiting constraint. If too high an amount of etherification zone raffinate is recycled in stream 45 to the FCC reactor 20, the fraction of paraffins in stream 35, containing n-olefins and iso-olefins, returning from the FCC zone to the etherification zone will be too high. This is because the paraffins do not react in the etherification zone and thus nearly all paraffins fed to the etherification are present in the etherification zone raffinate. Also, since the paraffins in stream 45 to the FCC reactor will not convert to iso-olefins and more paraffins are produced in the cracking process, this results in an ever increasing fraction of paraffins in stream 35.

Accordingly, an amount of the etherification zone raffinate must be bled via bleed stream 46 sufficient to maintain a desired fraction of iso-olefins in stream 35 to the etherification zone. Given this goal, for a given desired fraction of iso-olefins in stream 35, the method of calculating and engineering the appropriate recycle fraction of the etherification zone raffinate to the FCC reactor is conventional to one of ordinary skill in the chemical processing arts.

Figure 3:
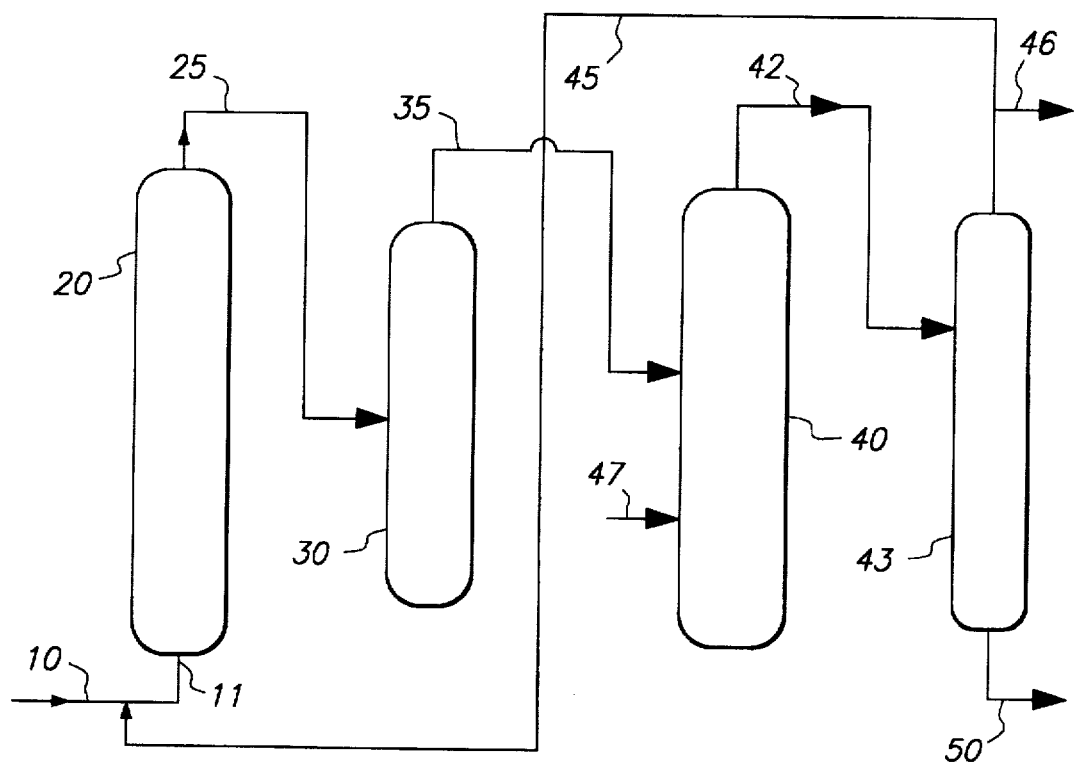
FIG. 3 depicts, in one embodiment, a schematic process flow diagram of the method of the invention where the etherification unit is followed by a distillation unit.

FIG. 3 is the same as FIG. 2, except that the etherification unit 40 is only a reaction unit and it is followed by a separation unit 43, typically a distillation column.

B. Process Conditions

The etherification zone, separation zone, and FCC zone each operate under conventional operating conditions, e.g., pressure, temperature, and flow rates. Such conditions are known in the art. Typical FCC conditions, e.g., are a temperature from about 425°–650° C., a pressure from about 0–6 atm., preferably from about 1.5–4 atm., a catalyst to feed weight ratio of 2:1–15:1, and catalyst residence time of less than about 3 seconds, typically about 0.3–3 seconds. Typical FCC conditions and catalysts are taught, e.g., in U.S. Pat. Nos. 4,368,114 and 4,340,465, the disclosures of which are incorporated herein by reference. A preferred catalyst for FCC reactions is an Ultrastable Y type zeolite. Typical isomerization conditions are taught, e.g., in U.S. Pat. Nos. 5,132,484 and 5,191,146, the disclosures of which are incorporated herein by reference. Typical etherification conditions are taught, e.g., in U.S. Pat. Nos. 5,387,723; 5,238,889; and 5,238,541, the disclosures of which are incorporated herein by reference.

ILLUSTRATIVE EMBODIMENTS

The following laboratory and pilot plant scale experimental results depict various embodiments of the method of the invention.

A. Embodiment 1:Effects of addition of 1 wt. % 1-Pentene And An Olefin Isomerization Additive To An FCC Feed

1. Overview

In this embodiment, a pilot plant scale FCC riser reactor was used. One weight percent normal pentene was added to the gas oil feed to the FCC reactor. The conversion of these normal pentenes to iso-pentenes was about 55 weight percent.

2. Detailed Description

A test was conducted in a 0.5 BPD circulating pilot plant equipped with a 29-foot riser. The catalyst was an equilibrium Y-zeolite-containing catalyst (OCTIDYNE-1770™, manufactured by Engelhard) plus 8% of a ZSM-5 olefin isomerization additive (or octane additive). The octane additive containing 15% ZSM-5 of $SiO_2/Al_2O_3$ molar ratio of 500. Run conditions included a reactor temperature of 950° F., a reactor pressure of 30 psig, and a catalyst/oil ratio of 10.8. The plant was run both with and without the addition of 1% 1-pentene to the gas oil feed. A summary of the results is given in Table I.

The GC analyses of the light gasoline showed that adding the 1-pentene to the feed produced an increase in $C_5$'s with no increase in higher carbon numbers. Looking at the incremental values listed in Table II, the increase in total $C_5$'s was 0.7 wt. % with an increase in etherable $C_5$ olefins of 0.38 wt. %, or 15 relative percent above the amount without pentene addition. About 55% of the incremental $C_5$'s went to etherable olefins.

TABLE I

Effects of addition of 1 wt. % 1-Pentene And An Olefin Isomerization Additive To An FCC Feed

| Run → | A | B |
|---|---|---|
| Product Composition ⇓ | | |
| Catalyst/Oil | 10.8 | 10.8 |
| + wt. % 1-Pentene | ~1 | 0 |
| 430° F. - Conversion Wt. % | 72.1 | 73.2 |
| ST-265° F., Wt. % | 27.0 | 27.4 |
| $C_5$ Total | 33.3 | 30.7 |
| $C_5$ Olefins | 17.2 | 15.2 |
| $C_5$ Paraffins | 15.7 | 15.1 |
| $C_5$ Olefins/$C_5$ Paraffins | 1.10 | 1.00 |
| $C_6$ Total | 29.6 | 30.5 |
| $C_6$ Olefins | 11.0 | 11.0 |
| N-$C_5$ | 1.82 | 1.67 |
| Iso-$C_5$ | 13.9 | 13.5 |
| 1-$C_5$= | 1.04 | 0.93 |
| T-2-$C_5$= | 2.95 | 2.66 |
| C-2-$C_5$= | 1.65 | 1.48 |
| 3M-1$C_4$= | 0.23 | 0.23 |
| 2M-1$C_4$= | 3.56 | 3.08 |
| 2M-2$C_4$= | 7.24 | 6.30 |

TABLE II

Incremental Effects Of Addition of 1 Wt. % 1-Pentene And An Olefin Isomerization Additive To An FCC Feed

| Product Composition | Incremental Increase In Weight Percent |
|---|---|
| Total $C_5$ | 0.70 |
| $C_5$ Paraffins | 0.16 |
| $C_5$ Olefins | 0.54 |
| Non-Etherable $C_5$ Olefins | 0.16 |
| Etherable $C_5$ Olefins | 0.38 |

B. Embodiment 2:Effects Of Addition of 1 Wt. % 1-Pentene To An FCC Feed Without Addition Of An Olefin Isomerization Additive This embodiment was done to test the effect of adding 1-pentene to a feed where the FCC catalyst was not combined with an olefin isomerization additive (or octane additive). Testing was carried out in a fixed fluidized bed laboratory unit operated at about 1000° F. with a catalyst/oil ratio of 7.1. The FCC catalyst was similar to the one of Embodiment 1. In this test, the effect of adding 5 wt. % 1-pentene was compared to the effect of adding 5 wt. % n-pentane (the paraffin should be unreactive). Results are listed in Table III.

The results show that 1-pentene addition increased $C_5$ olefins. Iso-$C_5$ olefins increased by 1.4 wt. %. About 37 wt. % of the $C_5$-olefin increase was to iso-olefins.

TABLE III

Effects Of Addition of 1 Wt. % 1-Pentene To An FCC Feed Without Addition Of An Olefin Isomerization Additive

| Component Added To Feed → | 5 Wt. % n-Pentane | 5 Wt. % 1-Pentene |
|---|---|---|
| Product Composition, Wt % ⇓ | | |
| $C_3$ Minus | 17.3 | 18.4 |
| $C_4$ | 20.0 | 20.3 |
| Iso-$C_5$ Olefins | 2.9 | 4.3 |
| n-$C_5$ Olefins | 2.4 | 4.8 |
| Isopentane | 7.1 | 8.3 |
| n-Pentane | 8.3 | 1.9 |

What is claimed is:
1. A method of making TAME, the method comprising:
   a. Passing an FCC zone effluent containing n-$C_5$ olefins and iso-$C_5$ olefins to an etherification-distillation zone, wherein at least a portion of said iso-$C_5$ olefins are converted to TAME;
   b. Recovering from said etherification-distillation zone an etherification-distillation zone raffinate containing n-$C_5$ olefins;
   c. Mixing at least a portion of said etherification-distillation zone raffinate containing n-$C_5$ olefins with an FCC feedstream, thereby forming a mixture and passing said mixture to an FCC zone containing a ZSM-5 zeolite having a $SiO_2/Al_2O_3$ mole ratio greater than about 500; and
   d. Contacting in said FCC zone, said mixture and said ZSM-5 zeolite having a $SiO_2/Al_2O_3$ mole ratio greater than about 500, under FCC conditions comprising a pressure from about 0 atm. to about 6 atm. and a temperature from about 425° C. to about 650° C., wherein at least a portion of said n-$C_5$ olefins in said mixture are converted to iso-$C_5$ olefins.

2. A method for skeletal isomerization of $C_{4-5}$ olefins, the method comprising contacting, in an FCC zone, at FCC conditions, an FCC catalyst with an FCC feedstock comprising a conventional FCC feedstock and an n-$C_{4-5}$ olefins-containing etherification zone raffinate, wherein at least a portion of said n-$C_{4-5}$ olefins are converted to iso-$C_{4-5}$ olefins.

3. The method of claim 2 further comprising contacting in said FCC zone, a ZSM-5 zeolite catalyst with said n-$C_{4-5}$ olefins-containing etherification zone raffinate.

4. The method of claim 3 wherein said ZSM-5 catalyst further comprises a $SiO_2/Al_2O_3$ mole ratio greater than about 40.

5. The method of claim 3 wherein said ZSM-5 zeolite catalyst further comprises a $SiO_2/Al_2O_3$ mole ratio greater than about 200.

6. The method of claim 3 wherein said ZSM-5 zeolite catalyst further comprises a $SiO_2/Al_2O_3$ mole ratio greater than about 500.

7. The method of claim 5 wherein said n-$C_{4-5}$ olefins and iso-$C_{4-5}$ olefins consist essentially of n-$C_5$ olefins and iso-$C_5$ olefins.

8. The method of claim 6 wherein at least about 25 mol percent of said n-$C_{4-5}$ olefins in said n-$C_{4-5}$ olefins-containing etherification zone raffinate are isomerized to iso-$C_{4-5}$ olefins.

9. The method of claim 4 wherein said FCC conditions comprise a pressure from about 0 atm. to about 6 atm. and a temperature from about 425° C. to about 650° C.

10. A method of making an ether selected from MTBE or TAME, the method comprising:

a. Passing an FCC effluent containing n-$C_{4-5}$ olefins and iso-$C_{4-5}$ olefins to at least one etherification zone, wherein at least a portion of said iso-$C_{4-5}$ olefins are converted to MTBE or TAME;

b. Recovering from said etherification zone an etherification zone effluent containing MTBE or TAME and n-$C_{4-5}$ olefins;

c. Passing said etherification zone effluent to a separation zone wherein at least a portion of said n-$C_{4-5}$ olefins are separated from said etherification zone effluent;

d. Mixing at least a portion of said n-$C_{4-5}$ olefins recovered in step(c) with an FCC feedstock, thereby forming a mixture and passing said mixture to an FCC zone containing an FCC catalyst; and e. Contacting in said FCC zone, under FCC conditions, said mixture and said FCC catalyst, wherein at least a portion of said n-$C_{4-5}$ olefins in said mixture are converted to iso-$C_{4-5}$ olefins.

11. The method of claim 10 wherein in step (d) wherein said FCC zone contains an ZSM-5 zeolite catalyst, and step (e) further comprises contacting said n-$C_{4-5}$ olefin and said ZSM-5 zeolite catalyst.

12. The method of claim 11 wherein said ZSM-5 zeolite catalyst further comprises a $SiO_2/Al_2O_3$ mole ratio greater than about 40.

13. The method of claim 11 wherein said ZSM-5 zeolite catalyst further comprises a $SiO_2/Al_2O_3$ mole ratio greater than about 200.

14. The method of claim 11 wherein said ZSM-5 zeolite catalyst further comprises a $SiO_2/Al_2O_3$ mole ratio greater than about 500.

15. The method of claim 12 wherein said n-$C_{4-5}$ olefins and iso-$C_{4-5}$ olefins consist essentially of n-$C_5$ olefins and iso-$C_5$ olefins, respectively, and said ethers consist essentially of TAME.

16. The method of claim 12 wherein said n-$C_{4-5}$ olefins, iso-$C_{4-5}$ olefins consist essentially of n-$C_4$ olefins and iso-$C_4$ olefins, respectively, and said ethers consist essentially of MTBE.

17. The method of claim 14 wherein at least about 25 mol percent of the n-$C_{4-5}$ olefins passed to the fluidized catalytic cracking zone in step (d) are converted to iso-$C_{4-5}$ olefins.

18. The method of claim 12 wherein said FCC conditions comprise a pressure from about 1.5 atm. to about 4 atm. and a temperature from about 425° C. to about 650° C.

* * * * *